United States Patent
Spichiger-Keller et al.

(10) Patent No.: US 6,409,909 B1
(45) Date of Patent: Jun. 25, 2002

(54) MODULAR SENSOR SYSTEM FOR THE INDUSTRIAL PROCESS MEASUREMENT TECHNIQUE

(75) Inventors: Ursula Spichiger-Keller, Au; Jürg Müller, Olten, both of (CH)

(73) Assignee: Eidgenossische Technische Hochschule Zurich, Zurich (CH)

(*) Notice: Subject to any disclaimer, the term of this patent is extended or adjusted under 35 U.S.C. 154(b) by 0 days.

(21) Appl. No.: 09/341,481

(22) PCT Filed: Jan. 13, 1998

(86) PCT No.: PCT/IB98/00044
§ 371 (c)(1),
(2), (4) Date: Aug. 16, 1999

(87) PCT Pub. No.: WO98/30892
PCT Pub. Date: Jul. 16, 1998

(30) Foreign Application Priority Data

Jan. 14, 1997 (CH) .................................... 64/97

(51) Int. Cl.[7] ........................ G01N 27/26; G01N 21/00
(52) U.S. Cl. .................... 205/777.5; 205/789; 205/787; 204/409; 204/403; 204/411; 422/58; 422/82.01
(58) Field of Search ................................ 204/400, 403, 204/409, 411, 412, 417, 415; 205/775, 777.5, 789, 787, 787.5; 422/58, 82.01, 82.05

(56) References Cited

U.S. PATENT DOCUMENTS

| | | | |
|---|---|---|---|
| 4,071,427 A | * 1/1978 | Cheng et al. | 204/419 |
| 5,462,880 A | * 10/1995 | Kane et al. | 436/138 |
| 5,571,396 A | * 11/1996 | Cormier et al. | 204/418 |
| 5,736,103 A | * 4/1998 | Pugh | 422/68.1 |

FOREIGN PATENT DOCUMENTS

| | | |
|---|---|---|
| DE | 4114959 | 11/1992 |
| DE | 4227569 C1 | * 9/1994 |
| EP | 0335859 | 10/1989 |
| EP | 0385964 | 9/1990 |
| EP | 0467479 | 1/1992 |
| EP | 0509791 | 10/1992 |
| EP | 0514575 | 11/1992 |
| EP | 0723020 | 7/1996 |

OTHER PUBLICATIONS

CAPLUS abstract of Warsinke et al. (DE 4227569 C1).*
Spichiger–Keller, U. E. "Prozessanalytik mit chemischen Sensoren", *TR Technische Rundschau HdA* (1997/1998), pp. 32–35.
Osswald, H. F., et al. "Flow–Through System of High Stability for the Measurement of Ion Activities in Clinical Chemistry" *Chimia*, vol. 31, No. 2 (Feb. 1977), pp. ?–?.
Schindler, J.G., et al. "Kontinuierliche ionenselektive und elektrochemisch–enzymatische Direktmessung am Menschen Hämoanalyse von Na+, K+, Ca++ und β–D–Glucose" *Chimia*, vol. 31, No. 10 (1977), pp. 404–407 Oct.

(List continued on next page.)

*Primary Examiner*—T. Tung
*Assistant Examiner*—Alexander Noguerola
(74) *Attorney, Agent, or Firm*—Ladas & Parry

(57) ABSTRACT

A modular, in particular multidimensional system for the reagent-free, continuous detection of a substance is disclosed. The system is characterized by the presence of at least two measurements modules of preferably different types. The modules are robust and designed for a long-time operation. They have an exchangeable or replaceable selective layer structure. The system may also include appropriate modules for amperometry and optical sensors.

23 Claims, 6 Drawing Sheets

OTHER PUBLICATIONS

Osswald, H. F., et al. On–line Continuous Potentiometric Measurement of Potassium Concentration in Whole Blood during Open–Heart Surgery, *Clinical Chemistry*, vol. 25, No. 1 (1979), pp. 39–43.

Oesch, Urs, et al. "Ion–Selective Membrane Electrodes for Clinical Use" *Clinical Chemistry*, vol. 32, No. 8 (1986), pp. 1448–1459.

Oggenfuss, P., et al. "Neutral–Carrier–Based Ion–Selective Electrodes" *Analytica Chimica Acta*, vol. 180 (1986), pp. 299–311.

Müller, Jürg, et al. "The sensor for all reasons" *Analysis Europa*, Oct. (1995) pp. 31–34.

Spichiger–Keller, U. E. "Inwiefern gleichen chemische Sensoren Sensillen?" *Vierteljahtsschrift der Naturforschenden Gesellschaft in Zürich*, vol. 141, No. 3 (1996), pp. 113–122.

Spichiger–Keller, Ursula E., et al. "8 Heiligenstädter Kolloquium, Prozessanlytik mit Chemischen Sensoren" *Technische Systeme Für Biotechnologie Und Umwelt*, Institute für Bioprozeβ–und Analysenmeβtechnik e. V. Heilbad Heiligenstadt (1996). pp. 200–206.

Spichiger–Keller, Ursula E. "CHemsens, 'The Lab in the Bag'", *Bio World*, vol. 4 (1997), pp. 4–8.

\* cited by examiner

MODULAR SENSOR SYSTEM FOR THE INDUSTRIAL PROCESS MEASUREMENT TECHNIQUE

CROSS-REFERENCE TO RELATED APPLICATIONS

This application claims priority of the Swiss application 64/97, filed Jan. 14, 1997, the disclosure of which is incorporated herein by reference in its entirety.

BACKGROUND OF THE INVENTION

The invention is related to process monitoring, especially a sensor system for the process monitoring technology, which allows the continuous and selective determination of various measured parameters.

STATE-OF-THE-ART

Sensor systems are known and described by the state-of-the-art.

The most well known systems for continuous monitoring are FIA-systems (flow-injection analysis). said systems consist of an extensive fluidics-system having pumps and valves. They make use of traditional analytical procedures using reagents and, occasionally, biosensors or ion-selective electrodes (ISE) at the end of the flow-system as detectors.

The known sensor systems are solely defined and specified by the application of potentiometric or voltammetric (electrochemical determination of the variation in the oxygen partial pressure) or amperometric or optical measuring techniques. The company YSI (2700 SELECT) offers an instrument equipped with biosensors for continuous process monitoring. The sensor elements are inserted into a miniaturized measuring chamber, which is filled with the specimen and evacuated therefrom. The amperometric and voltammetric systems involve biosensors and miniaturized modified electrodes such as "glassy carbon" or carbon Paste"graphite electrodes [compare Kalcher, K.; Kauffmann, J.-M.; Wang, J.; Svancara, I.; Vytras, K.; Neuhold, C.; Yang, Z. Electroanalysis 7/1 (1995) 5–22 (Review)]. Publications involve especially arrays (serial switch of a multitude of identical sensors, being identical with respect to their principle of function, on a geometrically defined sensor surface) using miniaturized sensors, so-called solid-state electrodes and ISFETs (ion-selective field-effect transistors) respectively [see Schindler, J. G.,: Schindler, M. M.; Herna, K; Reisinger, E.; Kulmann, U.; Graef, R.; Lange, H. Biomed Tech 36/11 (1991) 271–280, 282–284. (HCA 116:136186.; van der Schoot, B. H.; Jeanneret, S.; van den Berg, A.; de Rooij, N. F. Sensors and Actuators B 15/1–3 (1993) 211–213; [1] Hoffmann, W.; Rapp, R.; Ache, H. J.;

Stolze, D.; Neuhaus, D.; Hofmann, D.; Freywald, K. H. Micro Total Anal. Syst., Proc. $\mu$-TAS '94 Workshop, 1st (1995), in van den Berg, A.; Bergveld, P. (Eds). Dordrecht: Kluwer, Netherlands.

These systems lack on the one hand the ruggedness, especially of the structured layer and of the reference system, on the other hand, the flexibility, to integrate novel developments. Depending on the fabrication process, they can be optimized for a limited selection and limited number of types of selective layers only. Therefore, the applications are considerably restricted. Modifications of micro-structured sensor platforms are rarely advantageous and only if extremely large numbers of pieces can be produced. On the other hand, due to their unsatisfactory ruggedness and long-term stability, miniaturized sensors are primarily marketed as "one-way" sensors (i-STAT). This induces the production of waste of precious materials.

Continuous monitoring systems generally require the possibility of recalibration in order to guarantee a high reliability of the results. Nevertheless calibration-free systems were evaluated [Rumpf, G.; Spichiger, U. E.; Bühler, H.; Simon, W.; Anal. Sciences 8 (1992) 553–559.]

The selective determination of specific components of a mixture of substances is solely feasible upon applying so-called selectivity principles.

A large number of selectivity principles based on recognition molecules, such as selective ligands, or effective selectivity principles based on partition equilibria, are known [Fluka-catalogue "Selectophore™", 1996]. The development of some of these selectivity principles such as the magnesium-, nitrite-, heavy metal-selective ligands and layers have been considerably developed [Schaller, U.; Bakker, E.; Spichiger, U. E.; Pretsch, E. Talanta 41/6 (1994) 1001–1005; Spichiger, U. E.; Eugster, R.; Citterio, D.; Li, H.; Schmid, A.; Simon, W. In: S. Golf, D. Dralle, L. Vecchiet (Eds) "Magnesium 1993" London: John Libbey & Comp., 1993.]

Substance-selective ligands are dissolved in the bulk of a layer. Said layer or membrane often provides a satisfactory selectivity after a process of carefully optimizing the composition of the bulk medium. If such a layer is implemented into existing sensor elements by cast-in, gluing, photo-polymerization, and other polymerization procedures, a considerable loss in selectivity and sensitivity, respectively, has frequently to be accepted.

The process technique for casting layers and immobilizing of selectivity principles by photo-polymerization considerably limits the range of applications of selective layers and is not exploit the full potential of molecular recognition elements.

Despite of the large number of ligands and recognition elements, only few were incorporated into a layer and tested in analytical applications. Therefore, only single ligands were used in chemical sensors. The application of chemical sensors in analytical instruments has a fixed position only in medical applications since many years. Electrolytes are determined by automated instruments for daily routine, but also in "bed-side" analyzers or peripheral analyzers for the physician's lab, by using ion-selective sensors. The first instrument, which makes use of optical sensors, is on the market (OPTI, AVL Biosense Corp., Atlanta). The instrument is equipped with "disposable cartridges" and offers the parameters $pO_2$, $pCO_2$ and pH (based on fluorescence emission technology). In some instruments, a combination of biosensors (voltammetric or amperometric determination of the oxygen partial pressure, e.g. according to Olson, L. et al., Anal. Chim. Acta 224(1) (1989) 31 fe)) for lactate, glucose, peroxide, glutamate, creatinine combined with ion-selective electrodes are implemented. These combinations are based on miniaturized sensors making use of solid-phase transducers or semiconductor elements of type ISFET and ENFET (ion-selective-, enzymatic field effect transistors), where changes in the coulometric properties or the potential, respectively, at the gate are measured. Such a combination was marketed by "i-STAT" as a disposable sensor. These sensors exhibit the disadvantages of sensors as discussed before such as unsatisfying ruggedness and large amounts of waste.

A company selling since many years an amperometric glucose sensor ExacTech™ for self-monitoring, is MediSens Inc. (Waltham, Mass.) having a subsidiary in Basle; a coresponding instrument for industrial applications is the YSI glucose sensor of Yellow Springs (OH, USA). The sensors used in these instruments display several layers, which eventually provide for the selectivity of the biosensors. Each offered biosensor relies on the same electrode principle, which consists of the determination of the oxygen consumption by applying the traditional electrochemical oxygen electrode.

Since 1988, more than 1000 publications related to glucose biosensors have been published (see Gorton, L., Electroanalysis 7/1 (1995) 23–44). In contrast, optical sensors have hardly been introduced. The WPIDS (World Patent Index No) 95–256069 [34] describes the optical determination of straylight in living tissues, and WPIDS 93–213750 [26], the optical measurement of the blood hemoglobin content.

The objective of the present invention was therefore to provide a measuring system, especially for continuous process monitoring, which avoids the drawbacks of known sensor systems and sensors, and which is notably characterized by its high flexibility and ruggedness.

BRIEF SUMMARY OF THE INVENTION

The intended objective has been achieved by providing a continuous, modular, especially multidimensional, and rugged measuring system, which is ideally operated without reagents, as well as by providing special modular sensing elements and recognition systems suited to such sensor elements.

For the purpose of a better comprehension of the invention, some basic terms shall be defined hereafter:

pluridimensional (multidimensional), modular, continuous measuring system; sensor element; half-cell; measuring module; reference, reference module.

A continuous measuring system based on sensing elements presumes such sensors being reversible or being regenerable within the desired time-period, which means that their signal and the quantity generated, respectively, adapt to the short-term variations of the specific characteristics of the specimen. The measuring system may enable the continuous analysis through batch mode as well as through the flow-through mode. The term "modular" means that single sensors and sensor groups/-types/-procedures are implemented as sensor elements within single modules and may be combined as such in a system. The various sensing elements may be combined in rod-like modules, e.g. for reactor technology. Such modules are notably suitable for the flow-through. Characteristically, suitable dimensions of said modules allow to combine various measuring procedures within the same system. Therefore, the system becomes multidimensional, as the information describing a substance is yielded from orthogonal procedures. The term "multidimensional" describes the feature of the measuring system, which allows to combine sensor elements and measuring procedures in order to determine several substance in series or parallel. Two procedures, i.e. two different types of modules, may provide independent, i.e. orthogonal, information about the same substance and, therefore, increase the operational safety (e.g. an optical and potentiometric or optical and amperometric module). A module may also contain a half-cell or a reference element of a sensor element or more than a single sensor- or transducer element. Subsequently, where a specification shall be necessary, a module serving to measure will be termed "measuring module" independent of its function as a complete element or as a half-cell only, whereas a reference element or reference half-cell will be termed "reference module".

Ruggedness

Ruggedness generally describes the weak dependency of the generated quantity from minor variations of the parameters of the measuring system and the low susceptibility of a measuring technique or a -system to noise, including the long-term stability. The ruggedness may be further improved through automation of the analytical process and by automated recalibration.

Substance, target substance, target compound, analyte; group of target substances, background components.

A target substance or analyte is a substance or group of substances/class of compounds, which are involved in the process of yielding (physico-chemical) information. This information will mostly be used in order to quantify the substance in its medium and to yield a quantitative information, followed by decision making. The chemical sensing element or a group of elements is able to distinguish between the target substance or between groups of substances and the background components and are able to discriminate the background components.

Selective structured layer, selectivity principle.

Within the structured layer, the selectivity principle or recognition step, respectively, and the transducing step (see below) form a subsequent unit. The structured layer may consist of a single or of several layers, including layers having well-defined functions. They are referred to as a selective structured layer.

Selective recognition device; selectivity principle consisting of: recognition step; distribution equilibrium; partition; recognition component; reagent-free.

The recognition step leads to the typical selectivity of each sensor and sensor module, respectively. As a consequence of the selectivity principle, the target substance will be preferred against background substances. The selectivity principle may be based on distribution or partition equilibria and/or typical chemical interactions between target compound and at least one recognition component. The structured layer contains the relevant components of the chemical recognition process. As a rule, the selectivity principle may be reversible or regenerable within a time frame adapted to the continuous measuring system. The combination of these steps may be termed "selective recognition device".

Transducing Step

The transducing step involves a single step or a number of subsequent steps, which causes the generation of a quantifiable quantity upon inducing or triggering the selective recognition step and the selectivity principle.

Measured Quantity

The generation of the quantity results from the recognition process involving the specific selectivity principle, and from the subsequent transducing process. The measured quantity may be generated as a consequence of the changing partition equilibrium (potentiometry, IR-spectroscopy) or by coupling additives (e.g. an indicator) to the recognition step.

Information

After transducing and amplifying, the measured quantity is transferred to a data recording and processing system which generates the information on the target compound or on a group of target compounds. The measured quantity has to be referenced to a reference quantity in order to increase the reliability of the information. The information may consist in a qualitative but more frequently quantitative information, however it may contain validation and classification criteria.

The above defined terms are used in the following according to said defined meanings.

The modular system for continuous, reagent-free determination of a substance according to the invention is characterized by exhibiting at least two modules of identical or of different type for simultaneous yield of at least two informations, whereby each module contains at least one exchangeable (interchangeable) selective structured layer and a transducing device, whereby the layered structure enables a selective recognition step and allows for continuous monitoring. In a preferred embodiment of the measuring system, different modular types are combined, e.g. at least one ion-selective module and at least one module of another type etc. When combining three modules, one may contain a reference system. The reference system distinguishes itself from the measuring module in that it contains no selectivity principle or the selectivity principle being not active.

Further objects of the present invention are a process for the continuous determination of a substance, the use of the system as well as modules and recognition components that are adapted for the application within a measuring system. Specific embodiments are described in the dependent claims.

Reversible and also rapidly regenerable chemical sensors distinguish themselves through their capacity of continuos determination of a target component, the substance. In order to yield continuous information over a broad spectrum of substances, only FIA (flow injection analysis) has to be referenced as a comparable measuring technique. Contrary to chemical sensors, traditional chemical reactions using reagents are applied in FIA. The procedure distinguishes itself through a highly developed but cost-intensive Fluidics system.

The measuring system according to the invention is, contrary to existing measuring systems, distinguished by maximum flexibility, reagent-free operation and ruggedness against the characteristics of the specimen and against continuous long-term monitoring. Therefore, it may be applied for the monitoring of gases and volatile compounds. Through automation, the advantages according to the invention could be further improved. The flexibility is achieved, by the possibility of implementing basically all of the known sensor types, especially e.g. potentiometric and/or voltammetric measuring techniques may be combined with at least one other measuring technique, e.g. the amperometric and/or the optical one. The combination of such different measuring techniques makes it possible to provide a broad information base on one or several target substances. In addition, the combination of such different measuring techniques for identical target substances offers the greatest possible guarantee for reliable results of the measurements, especially for calibration-poor or -free systems. The selective layered structure, which is characteristic for each module and where both the recognition and transducing step occur, is forming the core of the sensor element. The ruggedness of the sensor element is guaranteed by optimizing the structure of the layer, by referencing, by automation, by the construction of the module and by the arrangement of the modules.

An essential feature of the system is therefore, that the selectivity principle, the selective structured layer, is exchangeable; it may be selected among a multitude of available layers and is, in view of a restricted lifetime, exchangeable. The selectivity principle, the selective layered structure, may be packaged cast on a support, and marketed in different sizes. Such a support may consist in the transducer simultaneously (e.g. planar wave-guide, planar or tube-like electrode, optical fiber, resonator, SAW-chip). The exchangeable selectivity principle may consequently be denoted as a chemically-active chip. The chemically active chip or chemochip is an important element of the measuring system. In addition, relevant features are that not only different sensors, but also various types of sensors may be connected as single modules in series or in any other arrangement. The arrangement in series is preferred in continuous flow monitoring (optimum throughput of specimens). The parallel arrangement is preferred for the determination of materials to be investigated that needs to be differently conditioned (pH, ionic strength, temperature etc.).

A module contains all the elements necessary as the basis of the selectivity principle, the molecular recognition step, the transducing step, the generation of the measured quantity and the transformation. As a consequence of its ruggedness, it is applicable repeatedly and continuously over an ex-tended-period of time. Owing to the special mode of implementation, the selectivity principle, the analyte-selective layer, may be calibrated with access from the side of the transducing element e.g. for measurements under sterile or aseptic conditions. This operation is feasible, as the transducing element is not necessarily inseparably connected to the structured layer.

The single module works reagent-free. Reagent-free operation means, that no assisting component is used as a reagent, which enables the chemical recognition step in addition to the selectivity principle. The modules according to the invention differ considerably from the FIA technique and similar continuous monitoring systems. Buffering, addition of a co-substrate or further conditioning agents are not defined as reagents and are, therefore, not excluded by the term reagent-free handling.

A single module may also consist of a single half-cell, another one can be the reference system, which is equally rugged and correspondingly long-term stable due to its high (buffer)-capacity. The combination of various autonomic sensor modules based on various function principles to one measuring system is named a multidimensional or pluridimensional system. Each module can be independent from another and contribute in an optimal way to the final information on the substance/s by an orthogonal contribution of information. The benefit for the user consists in the fact that he is not supposed to select a measuring technique, but he only decides on the analytical parameters and the target substances, respectively, he needs information and on the analytical performance that must be fulfilled. He may delegate to the supplier the decision concerning which measuring techniques, or sensor modules, to be combined under said circumstances. The same is valid for the decision on the number of measuring techniques and modules that have to be combined in order to achieve the given specifications and the highest possible operational security.

Experiences with various sensor technologies show that different principles exhibit different features, which are more or less suitable, but no single basic technology can cover a range of different applications with optimum performance. For instance, it was found that the optical measuring technique is especially attractive for the monitoring of dissolved oxygen (oxygen partial pressure in solution), and therefore is especially attractive to be used in modular sensors and sensor systems according to the present invention, owing to its simplicity and the quick response behavior. The optical measuring technique is therefore a valid alternative to electrochemical sensors. The optical measuring technique is in addition feasible for measurements of the sodium-, potassium- and calcium-, nitrite- and chloride activity as well as several uncharged target components and substrates such as alcohols, amines, glucose, humidity, lactate, etc. gases such as $NO_x$, $SO_2$, $NH_3$ etc within the specimen directly.

Particularly suitable calibration-free assays are e.g. the decay-time (luminescence decay-time) according to Draxler, S.; Lippitsch, M. E.; Klimant, I.; Kraus, H.; Wolfbeis, O.; J. Phys. Chem. 99/10 (1995) 3162–3167, and the symmetric measuring technique according to Rumpf, G.; Spichiger, U. E.; Bühler, H.; Simon, W.; *Anal. Sciences* 8 (1992) 553–559. The symmetric maesuring techniques e.g. according to Haase, A. E.; *"Investigation of the interaction between iono-selective liquid membranes and measured quantity in view of the continues monitoring of cations in blood" (Untersuchung der Wechselwirkung zwischen ionenselektiven Flüssigmembranen und Messgut im Hinblick auf die kontinuierliche Erfassung von Kationen im Blut)*. Diss ETH Nr. 10453 (1993) is adapted to prepare reference materials for the quality assessment of electrochemical determinations of the active molality of ions. Such reference materials/ quality control specimens are not available world-wide.

It has now been found that through such a symmetric measuring technique or by using symmetric membranes showing optimum compatibility with a specimen, respectively, and by using a symmetric arrangement of the measuring cell, reference materials for determining the molal activity of ions e.g. for quality assessment can be prepared. Reference materials are e.g. aqueous solutions of lyopilized blood plasma or -serum.

Especially for measurements in the pharmaceutical branch, in medical care and food technology, it may be necessary or recommended to sterilize the modules. In this respect, current state-of-the-art techniques may be cited, e.g. sterilization is referred to Haase, A. E.; *"Investigation of the interaction between iono-selective liquid membranes and measured quantity in view of the continues monitoring of cations in blood" (Untersuchung der Wechselwirkung zwischen ionenselektiven Flüssigmembranen und Messgut im Hinblick auf die kontinuierliche Erfassung von Kationen im Blut)*. Diss ETH Nr. 10453 (1993). X-ray sterilization of packed materials is feasible. In addition, it is necessary to avoid the contamination of measured specimens with toxic components. The toxicity of ISEs is described e.g. in Haase, A. E.; *"Investigation of the interaction between iono-selective liquid membranes and measured quantity in view of the continues monitoring of cations in blood" (Untersuchung der Wechselwirkung zwischen ionenselektiven Flüssigmembranen und Messgut im Hinblick auf die kontinuierliche Erfassung von Kationen im Blut)*, Diss ETH Nr. 10453 (1993). Amperometric systems based on the mediator TTF/TCNQ (tetrathiafulvalene-p-tetracyanoquinodimethane) are generally viewed as being toxicologically harmless.

BRIEF DESCRIPTION OF THE DRAWINGS

FIGS. 6A and 6B show the reaction path of the analysis of hypoxanthine, whereas FIG. 6A shows the oxidation procedure and FIG. 6B the reduction procedure.

Figure 1:
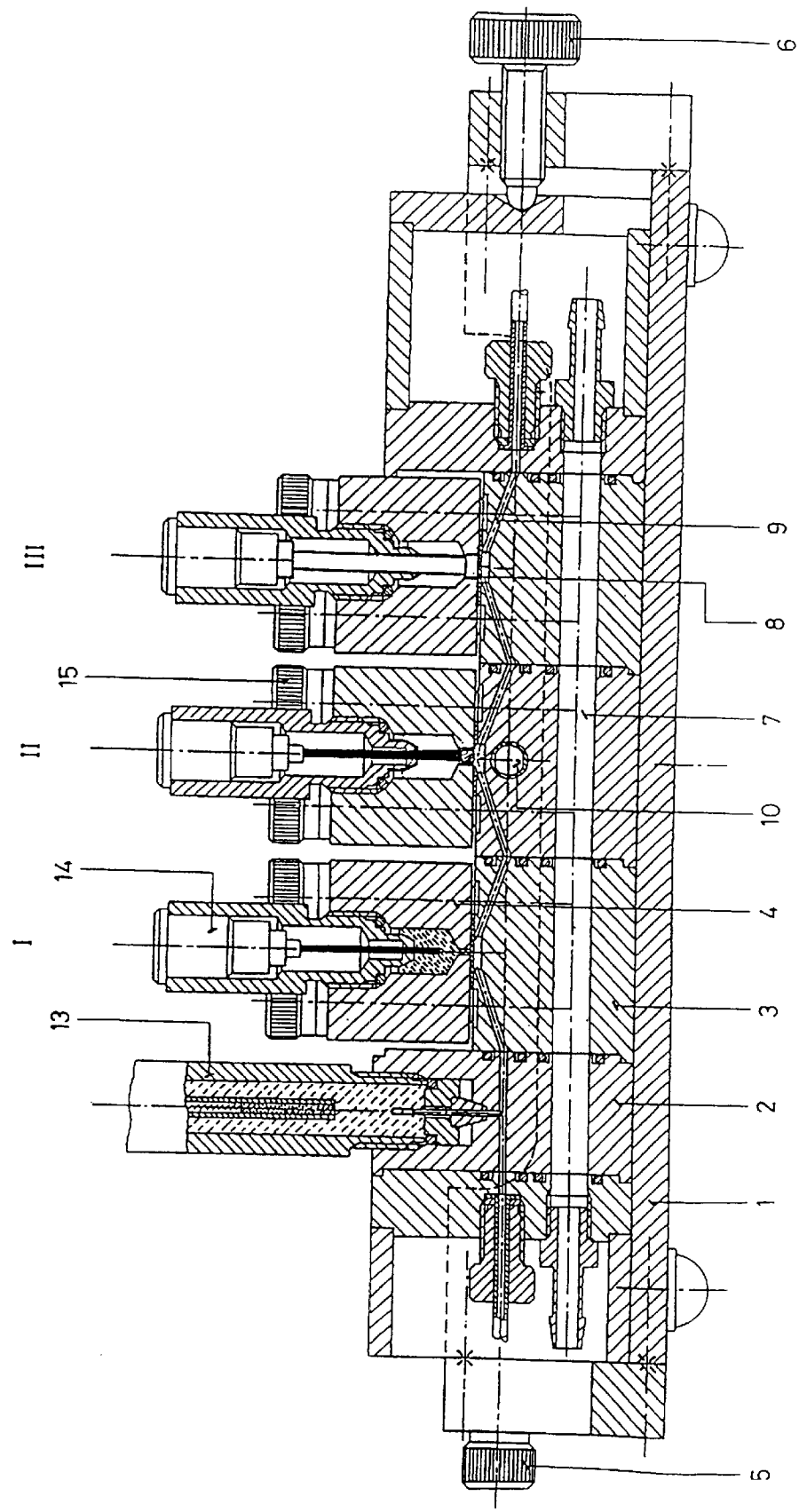
FIG. 1 represents in the longitudinal section an inventive modular three-dimensional system for the continuous process monitoring having a potentiometric, an amperometric and an optical selective sensor element.

The signs of the figures have the following meaning:

I: potentiometric module (half-cell), ion-selective sensor element

II: amperometric module (half-cell), biosensor module

III: optical module; fiberoptical module for fluorescence- or reflectance measurements.

1: Support of the flow-through system (e.g. from alumina)

2, 3, 4: Body of the electrode segments of the flow-through system (e.g. from polymethylmethacrylate) whereas

2 refers to the segment of the reference electrode, bottom piece

3 refers to the segment of the measuring electrode, bottom piece

4 Body of the measuring electrode, head piece

5, 6 Screws in order to fix the modules tightly against each other.

7 Flow-through channel for thermostated water

8 selective structured layer

9 sample or specimen channel

10 thermoelement

11 capillary with inner electrolyte

12 transducing device/element

13 Reference electrode/reference module (for potentiometric and amperometric half-cells)

14 Body of the transducing element/of the transducing device

15 Screw for connecting the membrane/selective structured layer tightly to the sample channel.

16 detection diode (on a plate)

17 emission diode

WAYS TO CARRY OUT THE INVENTION

The single module I, II, III, 13, which is suitable for a system according to the invention, consists of the body of the module 3, 4, which is manufactured from a polymer (see FIG. 1).

The body comprises an exchangeable (interchangeable) selective structured layer 8 and a transducing element 12 as well a, preferably, a channel 9 and, respectively, a tube for the continues and stop-flow transport of sample or specimen and for continuous monitoring. The body therefore comprises the sensing pad, where the selective structured layer 8 (e.g. ion-selective membrane; enzyme active paste, optode membrane, coated wave-guide, IR-wave-guide) on the one hand is in contact with the sample, where the recognition step takes place, and on the other hand with the transducing element 12, the transducing step, where the recognition step is translated into a quantity, which is transferred by the transducing device 12 (e.g. inner electrode, optical fiber, detector diode, amplifier and wire for the transduction of the electrical current) and is, optionally, compared with a reference quantity.

The module will be manufactured in a suitable size, preferably on the centimeter and micrometer scale. The single module can constitute an independent chemical sensing element or can consist of a half-cell (e.g. in potentiometry), whereby preferably a further module constitutes the second half-cell. Modules may be connected according to the needs and in any suitable arrangement (in series or parallel). Different modules are distinguished by their recognition- and/or transducing step, where a module is dedicated to and which discriminates one module from the other. Modules exhibiting the same transducing principle and therefore the same construction are assembled within identical modular types/module classes.

Types of modules which are distinguished by different measuring principles and, therefore, deliver different independent dimensions of the information about a substance (but which are constructed according to the same fundamental principle), such as e.g.:

- potentiometric half-cell with ion-selective membrane or combined potentiometric ion-selective electrode element
- selective amperometric biosensor element, e.g. having a selectivity inducing layer/paste
- element having a selective recognition step and a coated or uncoated optical planar wave-guide as a transducing or transfering element
- element having a selective recognition step and a transducing element for measuring absorbance, emission, and reflectance with coated or uncoated optical fibers
- selective "surface acoustic wave" sensing element
- conductometric sensing element having a selectivity principle
- capacitive sensing element combined with a recognition step
- optical or electrochemical reference element/half-cell.

Modules for potentiometry are well-known, nevertheless the advantages of an exchangeable structured layer were not realized. It was now found that potentiometric but especially amperometric and optical modules with exchangeable layered structure may be prepared and are useful for continuous monitoring technique and may be superior over permanently fixed layers.

The selective structured layer is the essential component of each module.

This comprises at least one component, which induces the selectivity of the sensing element, i.e. the preferred determination of the target substance and a group of target substances against background substances. The selectivity can be caused by molecular recognition of the target substance or by partition of the substance between sample/specimen and the sensing element (due to partition equilibria). The selective structured layer may contain additives, which enable the formation of the layer and/or which support the recognition step, catalyse and/or inhibit the influence of interferences, and optionally a further component, which is responsible for the transduction step. The structured layer comprises the possibility to combine the selective layer with assisting layers, which support e.g. the biocompatibility [compare Wintermantel E., Ha, S.-W. (Eds); Biokompatible Werkstoffe und Bauweisen (biocompatible materials and building modes, Berlin: Springer-Verlag, 1996] and/or enable the separation between gaseous, neutral and charged substances and/or create a diffusion barrier.

The structured layer may contain more or less lipophilic/apolar as well as more or less hydrophilic/polar layers as well as micelles or reverse micelles. Such structured layers were described for optical sensor elements in Vaillo, E.; Walde, P.; Spichiger, U. E.; Analytical Methods and Instrumentation, AMI, 2/3 (1995) 145–153. The leaching of components into the sample/specimen is avoided e.g. by a high lipophilicity of components, in the case where an aqueous sample/specimen is present [Dinten, O.; Spichiger, U. E.; Chaniotakis, N.; Gehrig, P.; Rusterholz, B.; Morf, W. E.; Simon, W. Anal. Chem. 63 (1991) 596–603.] or by immobilizing of single components.

The selective structured layer is, following to the invention, neither glued nor poured in with processes which decrease the selectivity and sensitivity, but preferably implemented into the system in its "native" form, which means in the form, in which it derives from the preparation. The sealing succeeds solely by the elasticity of the materials, especially of the structured layer. In all the systems described herein, this is feasible, by contacting the structured layer with the sensor module (e.g. by coating of the transducing device/transducing element) or by depositing it without any change or working on it. Therefore, a maximum selectivity and sensitivity is achieved.

The selective structured layer may be cast onto e.g. a planar wave-guide, an optical fiber, a reflecting layer, a diffusion barrier or deposited onto a support, and offered as a structured layer and deposited/positioned within a module. Among specialists, such layers are generally denoted as "disposable layers" or "disposable wave-guides with target-analyte selective layers". If a sensor element is consumed, either the selective element only, or the structured layer, but also parts of the module or the whole module may be replaced. The single module or a set of modules is preferably designed in a way to enable thermostatting and, therefore, following to its insertion into the system is ready for use.

At least one component of the structured layer brings about one target substance or one class of substances being preferably recognized by the sensor and generates a measured quantity. The Selective recognition may be induced by the partition equilibrium of the substance in favour of the structured layer or by a defined chemical interaction, by complexation, a reversible chemical reaction between target substance and a recognition component or a typical physical and spectral property, respectively.

As a recognition component, all natural and synthetic, as well as hybrid molecules can be employed. Such recognition components are for example enzymes, receptors, antibodies and its hybrids or fragments; carbohydrates, lactines, lipids, peptides, proteins and its hybrids or fragments: synthetic ligands, compounds that form hydrogen bridges, inclusion compounds, solubilisates, micelles, metal organic complexes, reaction products; carriers, ionophores, reactands and chromoreactands, redox indicators, electron donors and -acceptors, "charge-transfer"-compounds, pH-indicators, components for energy- and charge-transfer; macromolecules, organs, organellae, microorganisms.

The recognition step may be facilitated and favoured, respectively, by catalysts and additives (plasticizers as solvents, polymers and ions).

The target substance or class of target substances comprises a broad spectrum of compounds as a consequence of the combination of various detection systems. Some examples are: Application of the system according to claims 1 to 5 for the determination of inorganic and organic ions, charged, uncharged or neutral molecules, salts, isotopes, radicals, cells or cell components, organisms, microorganisms, viruses, organellae, or receptors within a sample.

The at least one transduction step leads to the generation of a measured quantity as the consequence of a physico-chemical process or upon coupling a second chemical tranduction process. The transduction step can comprise and combine more than one principle.

As a transduction step is denoted e.g. the generation of a frontier potential as a consequence of the recognition step/partition equilibrium. Further examples are: the generation of an electrical current subsequent to a redox process, spectral or frequency variations, changes in the resistance and the conductance, respectively, of the absorption or luminescence intensity, the polarity, the optical rotation, of the capacity, or changes in the mass, the number of particles and quantum yields, respectively, as a consequence of the recognition step etc. The quantity consists in counts, in the quantification of absorption, absorbance, emission or frequency changes, in changes of the current intensity (I), the potential (emf), or the conductance (σ), in changes of the mass (m), of the temperature (T), the decay time (t) or the lifetime ($t_{lim}$) etc. Said quantities are optionally transformed into e.g. concentration units and into an adapted language of information by calibration and by comparison with a reference, respectively.

In the following, some sensors and modules, respectively, are described by figures and examples. These figures and examples shall not limit the object of the invention in any way.

Multidimensional Modular Measuring System

FIG. 1 shows the arrangement of a measuring system (flow-through) with four modules I, II, III and 13, a potentiometric I and an amperometric II sensor module designed as half-cells, a module with reference element 13 (second half-cell), and an optical module III. The modules with transducer 12 are arranged vertical to a support 1. They are tightly fixed by screws 5, 6 arranged in parallel to the support 1. The flow-through channel 9 for the sample/specimen of a single module exactly joins the neighboured module and is sealed by e.g. a rubber seal to avoid any leaching.

The Potentiometric Module

Figure 2:
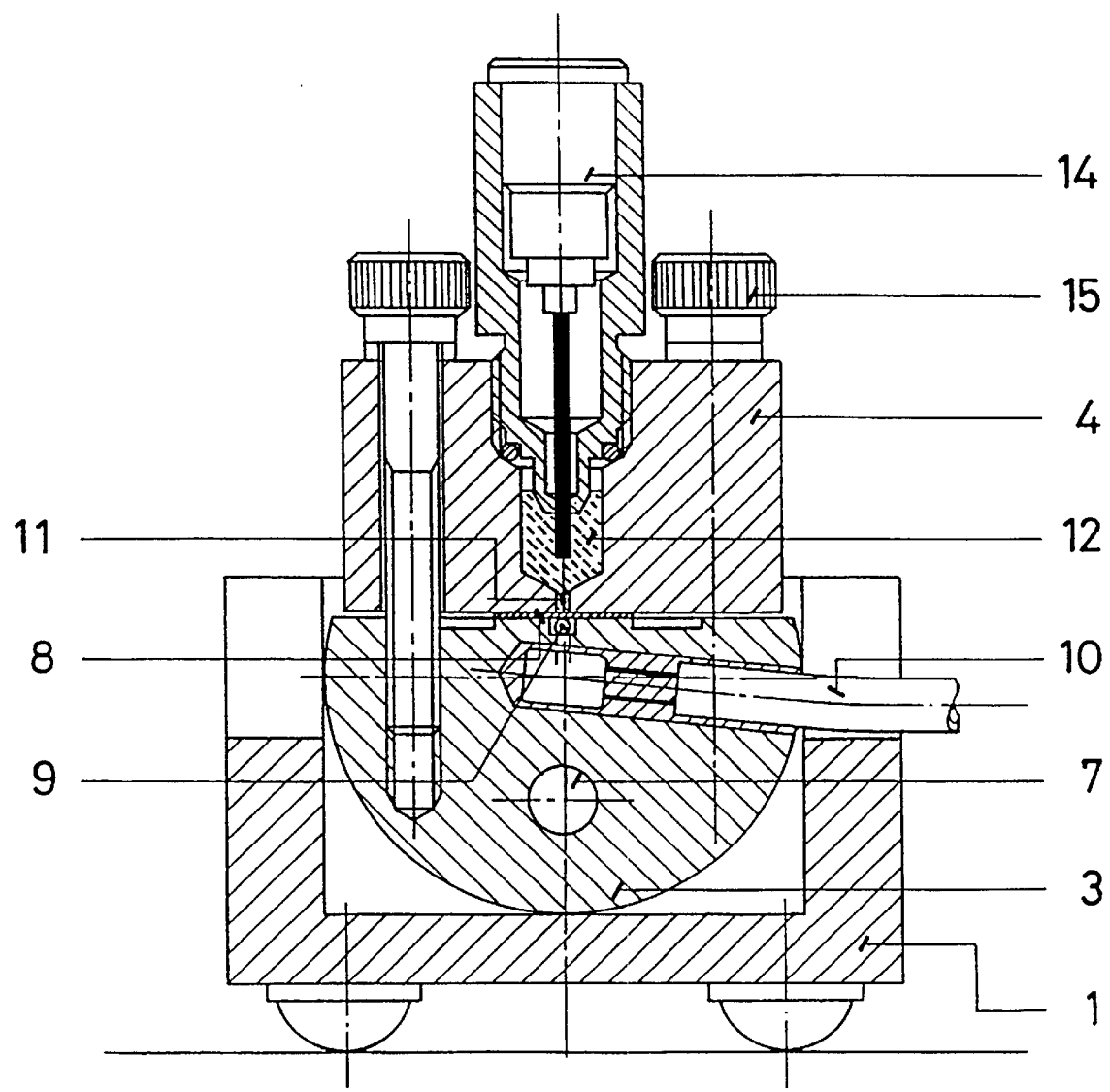
FIG. 2 shows a cross-section orthogonal to the longitudinal axis of the system of FIG. 1 through a potentiometric element having an exchangeable ion-selective membrane.

Within the potentiometric module I, the ion-selective layer is deposited onto the sensing pad and is contacted with the sample/specimen via the locally open sample channel 9 (see FIG. 1 and 2). In a specific case, the module is thermostatted with water 7; in place; a Peltier element may be implemented or the whole system may be thermostatted by air if desirable. The bottom piece 3 and the head piece 4 may for instance be produced independently from each other and, after positioning of the structured layer, be combined/fixed by means of fixing elements, e.g. screws 15. The head piece 4 contains the sensor element with structured layer 8 and the body of the transducer 14, and the tranducing element/transducing device 12, respectively, a transducing electrolyte and a transducing electrode is this case.

The head piece 4 is preferably designed in a way that only the type of sensor element selected, however, not the shape of the polymer-module is essentially modified. Thus, head and bottom piece may be produced in large numbers and, hence, in a cost-saving way. Furthermore, the exchange of modules and the flexibility of the system are guaranteed.

The Amperometric Module (Mediated Biosensor Electrodes)

Figure 3:
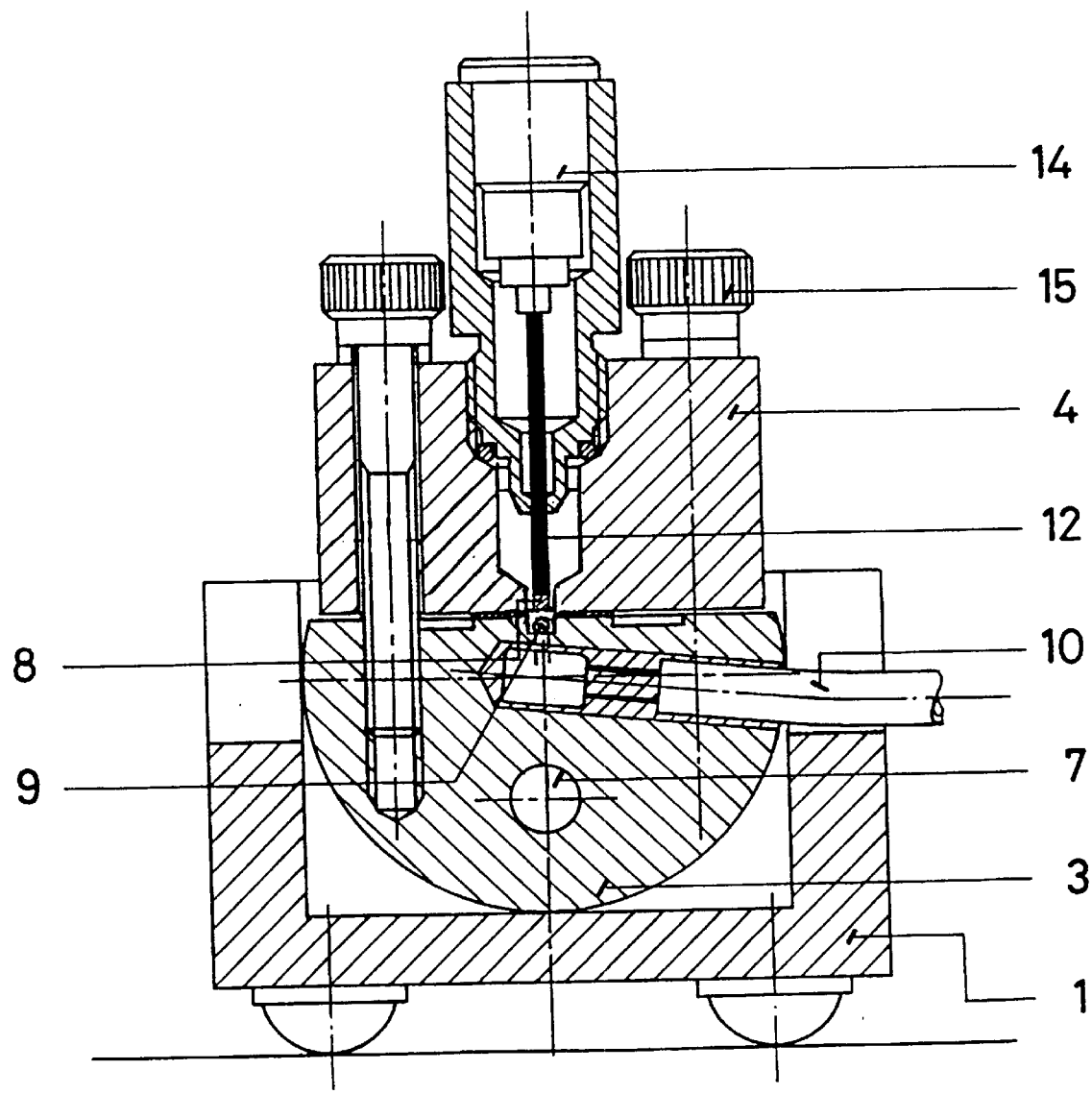
FIG. 3 shows a cross-section orthogonal to the longitudinal axis of the system of FIG. 1 through an amperometric module according to the invention, having a biosensor element.

It turned out, that an amperometric biosensor module can be constructed according to the same design as the potentiometric module (compare FIGS. 1 and 3). The ion-selective structured layer 8 of the potentiometric (ISE)-module is replaced by the structured layer 8 of the biosensor. The transducing element 12 herein consists preferably in a platinum wire which is in direct contact to the structured layer and the paste, respectively. The "paste" contains the enzyme as a recognition element, and preferably TTF/TCNQ (tetrathiafulvalene-p-tetracyanoquinodimethane) as a mediator and a bulk medium, e.g. silicon oil. Such pastes were described [see Korell, U.; Spichiger, U. E. Electroanalysis 6 (1994) 305–315]. The paste can be inserted within the head piece 4 in form of a tablet of adapted viscosity or combined with a support (e.g. from polyolefin), it can be cast onto the sensing pad or implemented in contact to the exchangeable electrode 12. In a preferred embodiment, the sample channel 9 constitutes locally of the counter electrode simultaneously. For example it consists locally of a platinum tube.

The reference module 13 is identical to that of the potentiometric module type. It preferably consists in a "free-flow free-diffusion" electrode (non-modular), as described in Dohner, R.; Wegmann, D.; Mort, W. E.; Simon, W. Anal. Chem. 58 (1986) 2585–2589.

This electrode turned out to be extremely rugged and poor in interferences under continues operation conditions.

The Optical Sensor Module

Figure 4:
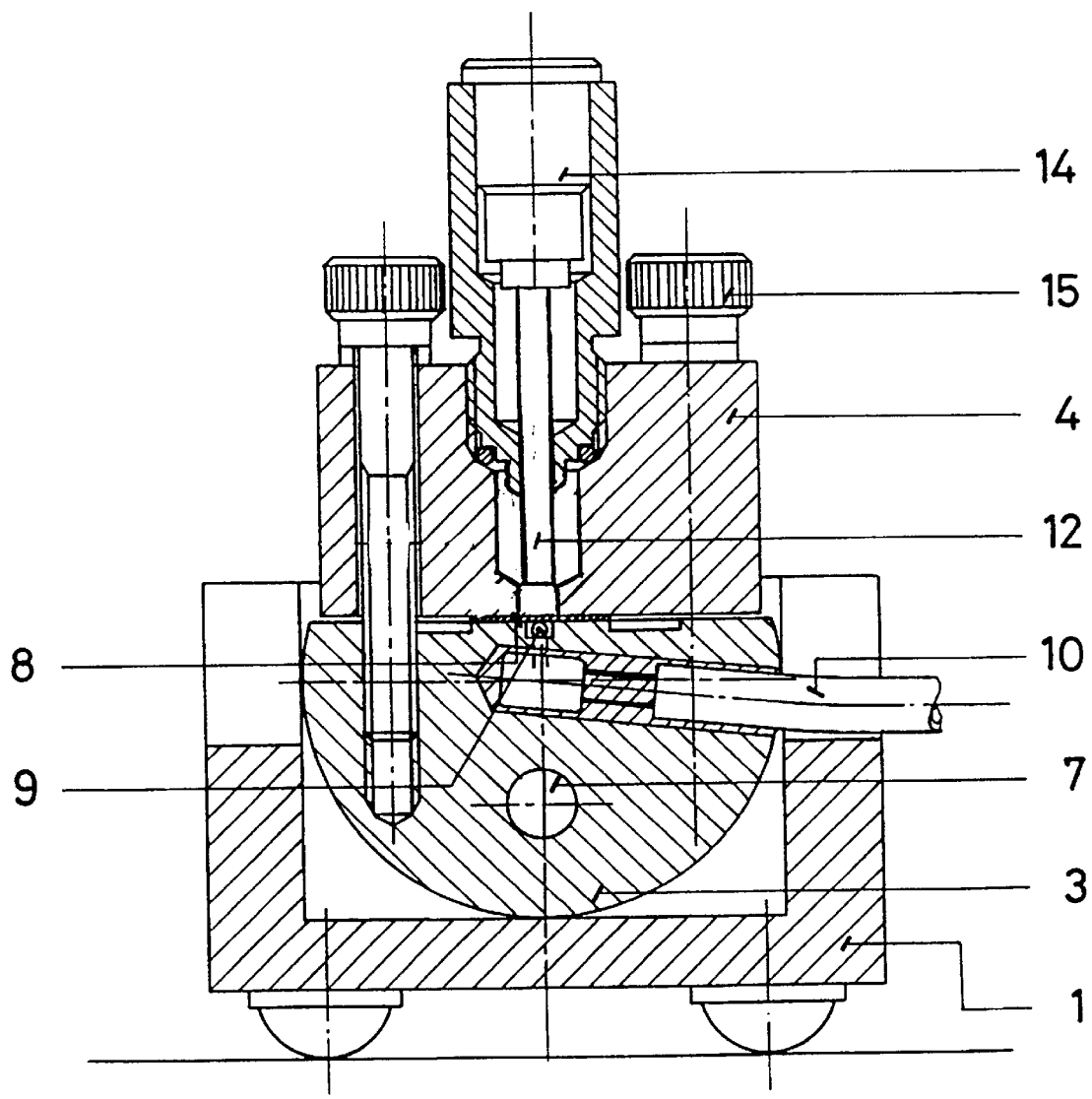
FIG. 4 shows a cross-section orthogonal to the longitudinal axis of the system of FIG. 1 through the optical module according to the invention having a fiber-optic element.
Figure 5:
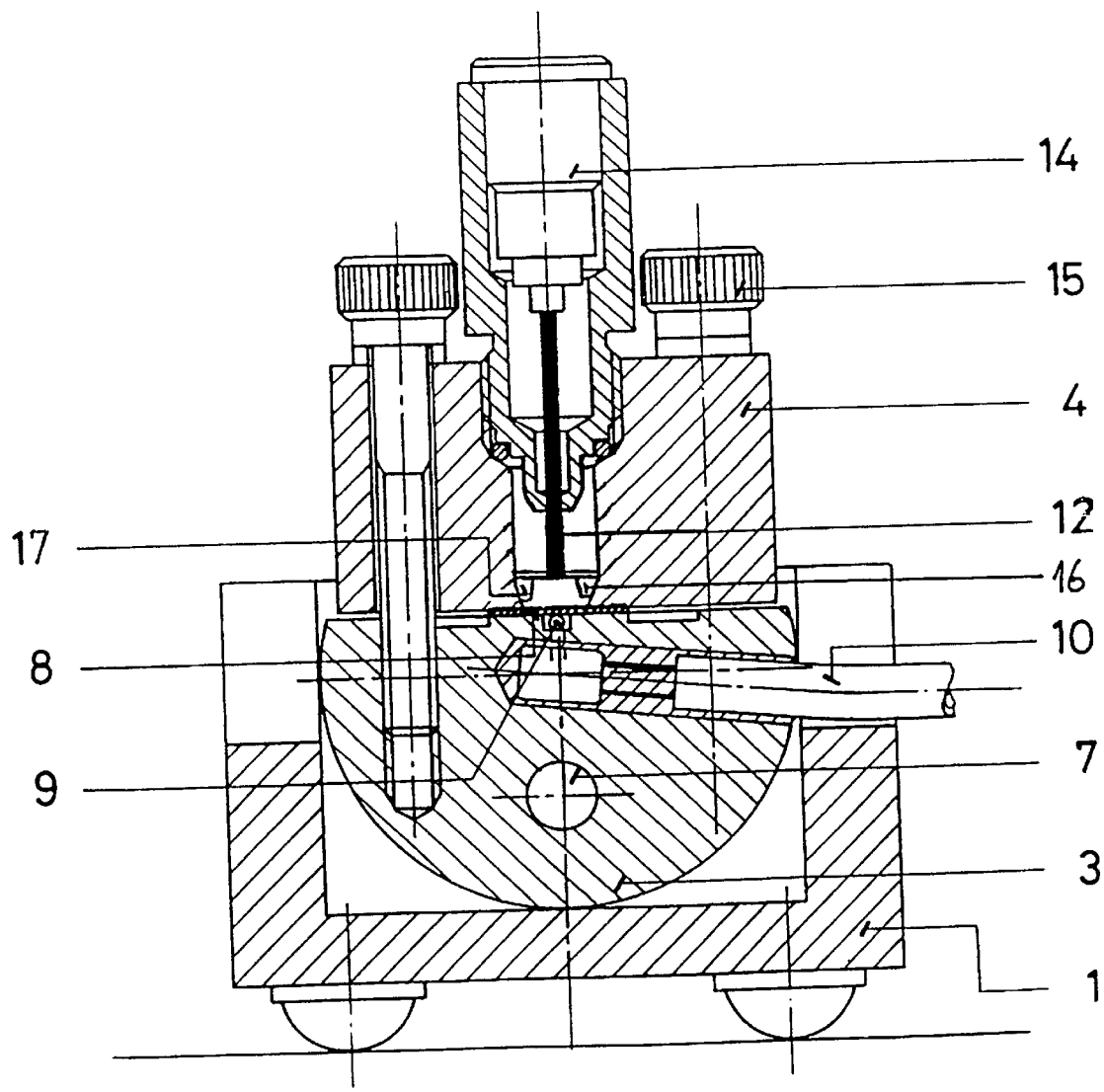
FIG. 5 shows a cross-section orthogonal to the longitudinal axis of the system of FIG. 1 through an optical module incorporating a diode element.
Figures 6A, 6B:
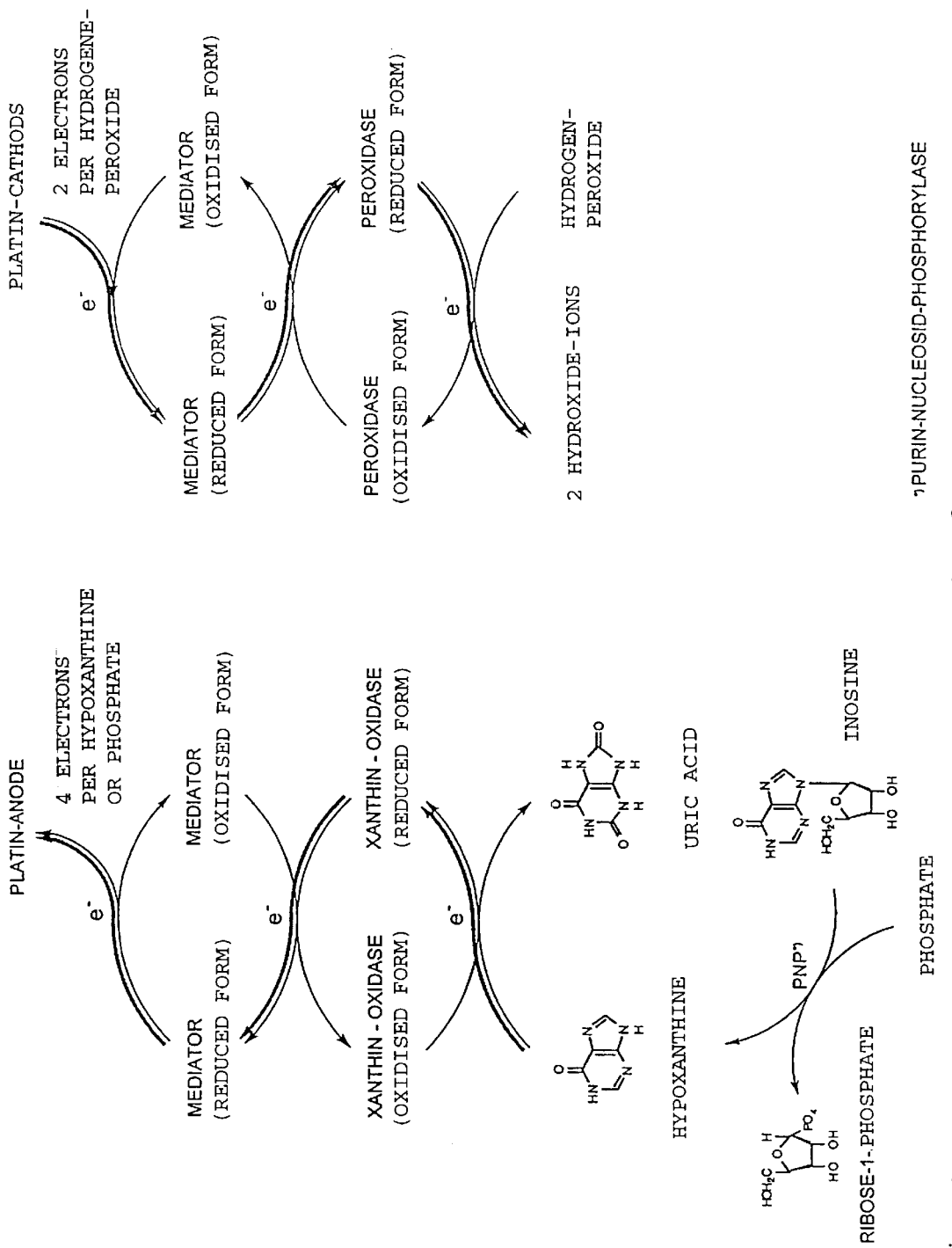

It was equally found, that furthermore optical sensors can be used for the continuous, rugged measuring technique. The design of the module according to invention is as follows:

The optical sensor module is constructed in a way that only the sensor elements (structured layer 8 and transducing device 12) in the head piece of the module vary (compare FIGS. 1, 4 and 5). Preferably, a disposable element shall be used as a wave-guide, where the structured layer is e.g. cast and at least one selectivity principle is realized/coupled to. The wave-guide can simultaneously enable the transducing step and, as a transducing device 12, be responsible for transduction. Wave-guides may be e.g. coated grating couplers, on which the selective structured layer 8 is cast onto the sensing pad or is deposited/incorporated into the head piece 4. For optical sensors, the quantity can be generated e.g. by measuring the absorption/absorbance in the ATR-mode (attenuated reflection) [compare Spichiger, U. E.; Freiner, D.; Lerchi, M.; Bakker, E.; Dohner, R.; Simon, W. SPIE Vol 1796 (1992) 371–382], by measuring the refractive index changes/variations [compare Freiner, D.; Kunz, R. E.; Citterio, D.; Spichiger, U. E.; Gale, M. T. Sensors and Actuators B 29 (1995) 277–285], by measuring of the optical rotation, the phase shift, the reflection or the luminescence decay time or by transducing the luminescence emission.

The incident light energy can be provided from outside of the module by an optical fiber or other optical wave-guides or the light source can be integrated by implementing diodes (emission diode 17, LED) into the head piece of the module (see FIG. 5). The transducing device 12 is for example an electrical cable.

In all these types of modules, the structured layer 8 and the transducing device 12 may be separated, which means that each of them is exchangeable. Hence, the multiple applications of the system are optimized and the costs are minimized. Through the very similar construction of the modules, they can ideally be combined, and enable the simultaneous and continuous measurement of various parameters of a sample.

Furthermore, it is possible to construct the transducing element 12 in an exchangeable way to body 14, in order to allow the exchange of this element, without exchanging a head section that contains possibly expensive electronics.

EXAMPLES

Recognition Components

Essential for each module is the selectivity principle or the recognition step, respectively, e.g. by a recognition component.

Potentiometry

Especially suitable recognition components for potentiometry are selective complexing agents. Some of them are detailed in the following:

The magnesium-selective complexing agents ETH 3832 and ETH 5506 have proved to be the most effective ligands of all [compare Spichiger, U. E.; Rumpf, G.; Haase, E.; Simon, W.; Schweiz. Med. Wschr. 121 (1991) 1875–1879; Spichiger, U. E.-, Electroanalysis 5 (1993) 739–745]. However, their optimum selectivity is related to an optimized composition of the layer or membrane [compare Spichiger, U. E.; Eugster, R.; Citterio, D.; Li, H.; Schmid, A. and Simon, W. (1994), Magnesium Activity Measurements: Facts and Enthusiasm. In: Golf, S.; Dralle, D.; Vecchiet, L. (Eds), *Magnesium* 1993, London: John Libbey & Comp. Ldt., pp.49–60]. The currently optimum composition is the following:

Ligand ETH 3832 or ETH 5506 1–2 wt % plasticizer ETH 8045 approx. 62 wt %

KTpClPB (potassium tetrakis[3,5-bis(trifluoromethyl) phenyl]borate) 155 mol % relative to the ligand PVC and hydroxy-PVC, respectively approx. 35 wt %

The ligands are described in Spichiger, U. E.; Eugster, R.; Citterio, D.; Li, H.; Schmid, A. and Simon, W. (1994), Magnesium Activity Measurements: Facts and Enthusiasm. In: Golf, S.; Dralle, D.; Vecchiet, L. (Eds), *Magnesium* 1993, London: John Libbey & Comp. Ldt., pp.49–60 and O'Donnell, J.; Hongbin, L.; Rusterholz, B.; Pedrazza, U.; Simon, W., Anal. Chim. Acta 281 (1993) 129–134. The plasticizers according to Eugster, R.; Rosatzin, T.; Rusterholz, B.; Aebersold, B.; Pedrazza, U.; Rüegg, D.; Schmid, A.; Spichiger, U. E. and Simon, W. Plasticizers for liquid polymeric membranes of ion-selective chemical sensors. Anal. Chim. Acta, 289 (1994) 1–13. Instead of ETH 3832 other lipophilic, highly alkylated derivatives may be used such as e.g. the dodecyl derivative ETH 5405 (Spichiger, U. E., Electroanalysis, 5 (1993) 739–745). Instead of ETH 9045 as a plasticizer, ETH 5373, ETH 220 and others may be applied.

In order to prepare the selective layer, the components are dissolved within a volatile organic solvent (e.g. THF, chloroform, methylenchloride, cyclohexanone and mixtures). The selective layer is prepared according to Oesch, U.; Brzozka, Z.; Xu, A.; Rusterholz, B.; Suter, G.; Pham, H. V.; Welti, D. H.; Ammann, D.; Pretsch, E.; Simon, W. Anal. Chem. 58 (1986) 2285. The layer/membrane may be coated in order to increase the biocompatibility of the surface e.g. with a polyurethane preparation dissolved in THF. For that, the membrane is dried on a glass plate. The glass plate e.g. having a 1.8 cm diameter, is fixed on a disk rotating at 600 to 1000 rpm. Now, 0.5–1.0 ml of a solution with 0.3 to 3.0 wt % polyurethane (e.g. Tekoflex EG-80A, EG-85A (Thermedics, Woburn)) are applied by a syringe and dried. In this way, a structured layer having favourable properties is prepared. The advantage of this treatment is, that a surface which is rugged against adsorptions from the biological specimen is created, without changing relevantly the properties of the selective layer or its response time.

Any modification of the composition can induce a partial loss in selectivity and sensitivity. A synthesis for the ligand ETH 5506 is described in O'Donnell, J.; Hongbin, L.; Rusterholz, B.; Pedrazza, U.; Simon, W., Anal. Chim. Acta 281 (1993) 129–134. This includes several side products, which have to be purified chromatographically. The synthesis was therefore simplified by the following steps.

Deprotecting the 1,3,5-tris(aminopentyl) benzene by reduction of the phtalide to the triamidetriol (NaBH4, i-PrOH/H2=17/3; 12 h RT) having 92% yield and pyrolysis of the triamidetriol (170–200° C., 4 atm in the bulb tube) with subsequent distillation of the triamine (200° C., high vacuum within the bulb tube) in the same step with 95% yield.

Also the synthesis of the 4-nitrophenylester activated 1-adamantyl-methyl-malonmonoamide-building block was designed more efficiently. The synthesis of the adamantyl amine from N-adamantylmethyltrifluoroacetamide results in poor and non-reproducible yields of the sec. amine. This problem was resolved by hydrolysing the trifluoroacetamide with KOH/18-crown-6 in THF. As an educt, the much cheaper adamantylhydrochloride was used and methylated with methyliodide. The methylated adamantylamine was continuously reacted in reflux with malondimethylester to yield the adamantyl-methyl-malondiamide. The product precipitated from the mother liquor and can be filtered (yield of 80%). Unreacted adamantyl-methylamine can be re-isolated. The 1-adamantyl-methyl-malonamide building block activated as the nitrophenylester is obtained with a yield of 40% following to both steps.

Ligands for the determination of heavy metals, especially lead:

For the determination of lead in drinking-, ground- and wastewater, lipophilic 19-di- and trithia-crown-6 isologues were developed as $PbOH^+$-selective ligands. Ligands developed before showed a selectivity for copper which was insufficient for the analysis of water samples and did not allow the selective analysis of lead ions [Lerchi, M.; Bakker, E.; Rusterholz, B.; Simon, W. Anal. Chem. 64 (1992) 1534-; KTI-Projekt Nr. 2692.1; EUREKA-Projekt "ASREM" EU 1013]. The ligands 18,18-bis-(dodecyloxymethyl)-1,4,13, 16-tetraoxa-7,10-dithiacyclononadecan (5) and 18,18-bis-(dodecyloxymethyl)-1,7,10,16-tetraoxa-4,13-dithiacyclononadecan (7) were synthesized and incorporated into classical ion-selective PVC-membranes containing ethyl-hexylsebacate (DOS) and dibutylsebacate (DBS), respectively, as a plasticizer and 30 mol % potassium tetrakis[3,5-bis(trifluorometyl)-phenyl] borate. The selectivity patterns of both ligands were investigated potentiometrically using the separated solution method (SSM) according to IUPAC. They are characterized by a discrimination of copper ions by a factor of $10^{-5.8}$ and by a discrimination of alkaline ions of a factor of $>10^{-3}$ (molal concentration units). Even here, a relevant contribution of the plasticizer and the medium, the environment, respectively, was observed. Preferred plasticizers or media are ETH 8045, ETH 220 [described in Eugster, R.; Rosatzin, T.; a.a.O. S 26, line 27], bis(2-ethylhexyl) adipate (Fluka Chemie AG, Selectophore).

Synthesis and Application of Chromogenic Ligand for Carbonate, Humidity and Primary Alcohols Various trifluoroacetaniline derivatives were prepared by Keller-Lehmann, B.; Diss ETH Nr. 9255. Trifluoracetophenon-Derivate als carbonatselektive Ionophore in PVC-Flüssigmembran Elektroden (trifluoroacetophenone-derivatives as carbonate-selective ionophores in PVC liquid membrane electrodes) (1990) and proposed as reactive recognition elements for the selective determination of carbonate, humidity and primary alcohols. The recognition reaction consists in the generation of the hemiacetal and is reversible. The ligands were successfully incorporated into optode and electrode membranes (compare Wild, R.; Citterio; D.; Spichiger, J.; Spichiger U. E. J. Biotech. 50 (1996) 37–46). For the detection in optical sensors, the decrease in absorbence of the aromatic trifluoroacetyl group as a consequence of the generation of the hemiacetal at a wavelength of 305 nm is observed. This wavelength, however, is not suitable for constructing mobile, low-cost sensor elements. Therefore, a group of chromogenic reactands was developed, which absorb in the visible range of the spectrum and, nevertheless, preserve the selectivity in view of the mentioned substances. These are N,N-disubstituted-aminophenyl-4'trifluoroacetyl-azobenzenes, N,N-disubstituted aminonaphtyl-4'-trifluoroacetyl-azobenzenes, 4-trifluoroacetyl-4'-(N,N-disubstituted-amino)stilbenes and disubstituted-p-amino-trifluoroacetyl-stilbenes, such as N,N-dioctylaminophenyl-4'-trifluoroacetyl-azobenzene, N,N-dioctylaminonaphtyl-4'-trifluoroacetyl-azobenzene, 4-trifluoroacetyl-4'-(di-N-octylamino)stilbene and p-di-alkylamino-trifluororacetylstilbene. These are prepared according to schemes 1 to 3. The synthesis of the stilbene derivatives takes place from 1-iodo-4-alkylaminobenzene and 1-bromo-4-ethenylbenzene with subsequent acetylation with trifluoroacetylmethylester. The substituents are long-chained and lipophilic. They are distinguished by their electron-inducing effect. Usually their lipophilicity is at least 3 according to Hansch.

The chromophoric reactands are linked covalently e.g. to acrylate and methacrylate and may be immobilized within polymer membranes.

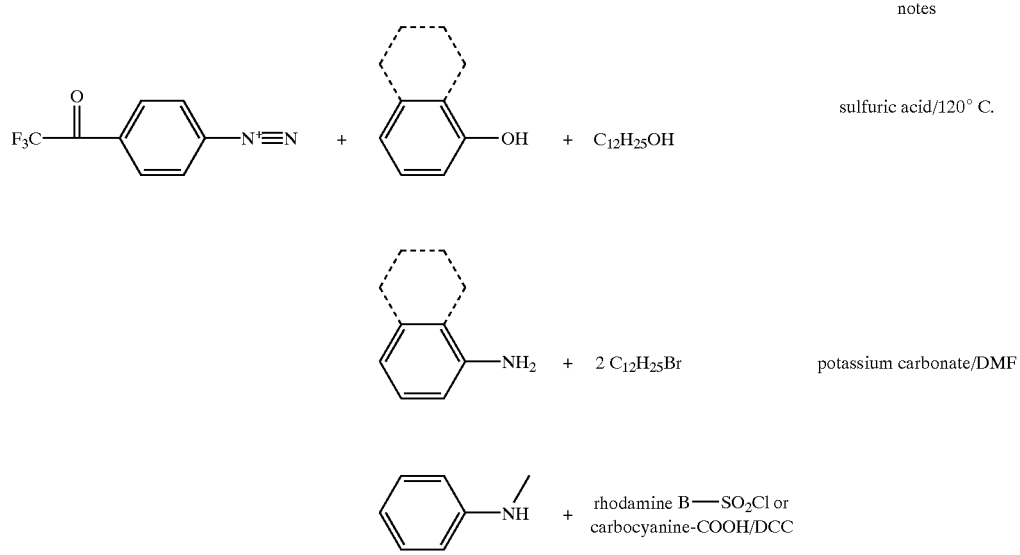

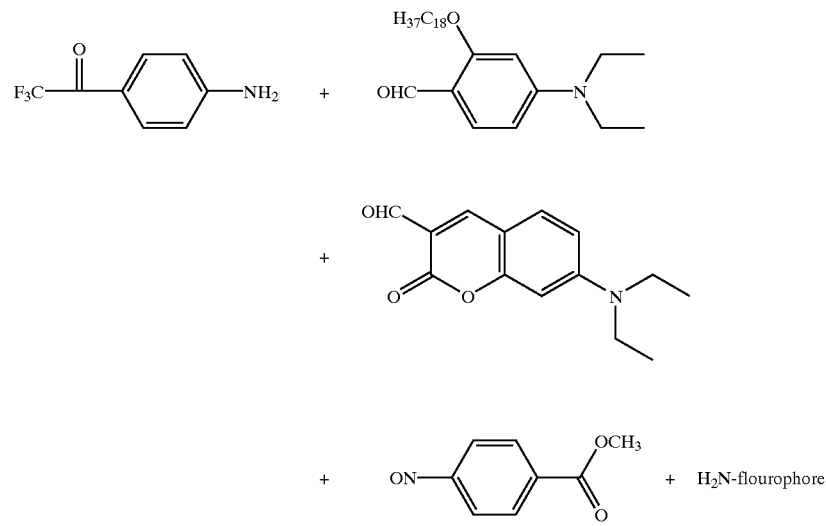

Scheme 3

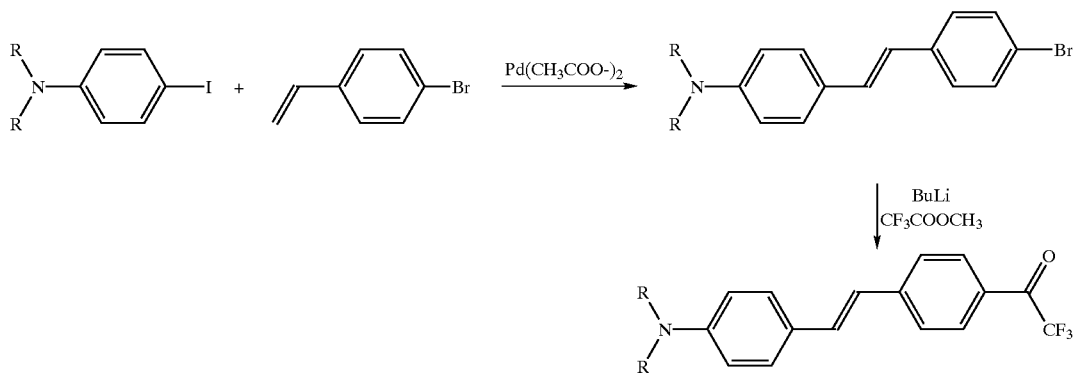

Preparation of Optical Selective Layers for the Determination of Nitrite, $NO_x$ and Chloride.

On the basis of known nitrite-, $NO_x$—and chloride-selective ligands (nitrite ionophore I, Fluka Chemie AG, Buchs, Schweiz; chloride-selective ligand ETH 9033 [compare Rothmaier, M; Quecksilberorganische Verbindungen als neutrale Anionencarrier in ionenselektiven PVC-Fl ussigmembranen (mercury-organic compounds as neutral anion carriers in ion-selective PVC-liquid membranes) Diss. ETH Nr. 10812, 1994], layers/membranes for optical sensor elements were prepared. Therefore, a chromoionophore (chromoionophore I, II, VI for nitrite; chromoionophore III for chloride, Fluka Chemie AG, Buchs, Schweiz) was dissolved within a DOS-plasticized PVC-layer together with nitrite- and chloride-selective ligands, respectively, and, where charge-compensation is necessary, together with anionic and cationic, respectively, lipophilic additives. The changes in absorbance as a consequence of co-extraction of an anion together with $H^+$ from the pH-buffered sample solution is determined photometrically and correlates with the concentration changes of the anion.

For nitrite, the dynamic range lies between 0.24 and 5000 mg $kg^{-1}$, chloride is discriminated with a selectivity factor of $10^{-2.9}$ (molal units). The measuring range and, depending on the dynamic range, also the response velocity vary with the applied chromoionophore; the chromoionophores show different stability. The implementation of several optode layers for the determination of nitrite or of a nitrite-selective optode and electrode within the same system can, according to the issue, be desirable. The nitrite-selective membrane with chromoionophor VI as a indicator shows luminescence in the visible range of the spectrum and can therefore be used as a luminescence-active layer.

The above mentioned ligands, have preferred application areas, nevertheless, they may generally be applied as selectivity principles in optical, potentiometric and other systems of free-choice, optionally in combination with further layers, optionally for the determination of gases and volatile substances.

Determination of Oxygen with Optical Sensors

Especially for oxygen determination with optical sensors a novel selective system was developed.

Ru(II)-complexes with organic ligands, especially Ru(II)-(4,7-diphenyl-1,10-phenanthrolene)$_3$ complexes were introduced in the last years for the determination of the oxygen partial pressure in solutions. The Ru(II)-complex serves simultaneously as a recognition and transduction component. Thereby, the fact that the luminescence emission of the complex is quenched i.e. suppressed by oxygen is exploited. The excitation occurs at 470 nm, the emission lies at 607–624 nm, depending on the medium/bulk of the layer.

The known Ru(II)-complexes are very hydrophilic, despite of the association to an organic ligand, and are hardly soluble within an apolar layer. Only by introducing lipophilic groups at the phenyl moiety, for example by alkylation of the phenyl residue in 4'-position, this became possible. Particularly, propyl- to dodecyl, more preferably propyl- to octyl-, and most preferably propyl- to heptyl-derivatives within the apolar membrane environment are appropriate indicators for dissolved oxygen. The leaching out can be additionally slowed-down by ion pairing with lipophilic anions and by immobilization, respectively. Such complexes are synthesized in 3 steps according to scheme 4 and subsequent purification process. The preparation of 4-heptyl-β-chlorpropiophenone [according to Case, F.; Strohm, P. F.; J. Org. Chem. 27 (1962) 1641 ff.] took place from 1-phenylheptane and 3-chloropropionic acid chloride, the preparation of 4,7-bis(4'-heptylphenyl)-1,10-phenanthroline according to Lund, G. K.; Holt S. L.; J. Org. Chem. Eng. Data, 26 (1981) 277 ff.] from 1,2-phenylenediamine and 4-heptyl-β-chlorpropionic acid, and the synthesis of the Ru(II)-complexe, Ru(II) [4,7-bis(4'-heptylphenyl)-1,10-phenanthrolene]$_3$ according to Wolfbeis, O.S.; et al., Anal. Chem. 60 (1988) 2028 ff.] from (4'-heptylphenyl)-1,10-phenanthrolene and $RuCl_3$.

Scheme 4

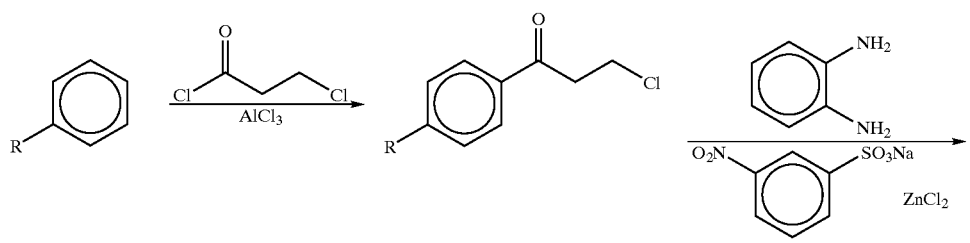

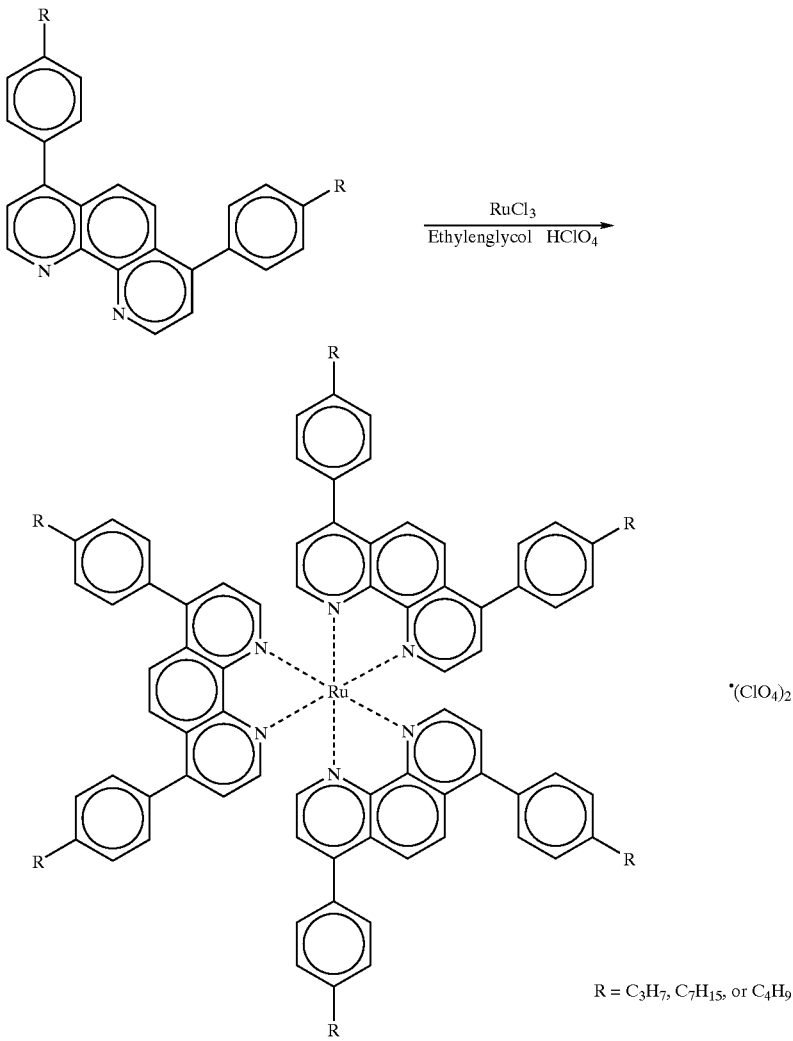

The purification took place with hexane/water, acetone/water and activated carbon, recrystallisation from acetone/water column chromatography with dichlormethane/acetone or chloroform.

The analogous synthesis of the propyl- or butyl derivative is performed starting from 4-propyl-β-chloropropiophenone and 4-butyl-β-chloropropiophenone, respectively.

The excitation in modules according to the invention is preferably made by using wave-guides or diodes within the head piece of the sensor module. The luminescence emission is derived in the same way. The measured quantity and the measured signal, respectively, are generated based on the change in the emission intensity at 607 to 624 nm. The measured quantity is compared with the signal of a solution with known $O_2$-partial pressure, which leads to the information about the target substance.

Furthermore, the life expectancy of the luminescence emission in plasticized polymers was investigated. Good results were obtained. The determination of the decay time is especially suitable in order to realize calibration-free systems. Complexes of the discussed ligands with lanthanides (e.g. Eu, La) allow to create other attractive compounds with extended life expectancy for the measurement of the luminescence decay-time.

The use of Ru(II)-complexes within an organic phase of reverse micelles [compare Vaillo et al; AMI 2/3 (1995) 145–153] leads to simple and direct indicator layers for the determination of the activity of oxidases (e.g. for lactate, glutamate, glucose oxidase, hypoxanthine, peroxidase) e.g. making use of the oxygen consumption.

Contrary to earlier selectivity principles, consisting of 2 layers that were prepared according to the detrimental state-of-the-art techniques described before, the single-layer system is more efficient and, therefore, more rugged against the variable oxygen-pressure.

Amperometric Biosensors

A component of the selective structured layer of an amperometric biosensor is e.g. a paste, which contains an organic mediator as an electron transfer catalyst, and is prepared according to Korell, U.; Spichiger, U. E. Electroanalysis 6 (1994) 305–315; Korell, U.; Spichiger, U. E. Anal. Chem. 66 (1994) 510–515. The redox-active enzyme is integrated into the paste and shows an optimum life expectancy within this environment. The "bulk" of this paste serves as a reservoir for the supply of the active enzyme. The paste may be incorporated into the provided recess in the head piece of the sensor module (see FIGS. 1 and 3). The surface constitutes the sensor field where sample and selective structured layer contact each other. Preferably, the paste is highly viscous and elastic, and therefore, may constitute a tablet, or is deposited within a support as an exchangeable tablet.

Glucose Determination

A paste containing 20 wt % glucose oxidase (GOD EC 1.1.3.4) in silicon oil/TTF/TCNQ, was operated continuously over 2.5 months (standard parameters; T 25° C.; operating voltage U=+200 to −200 mV; pH-buffer: 50 mM imidazole/50 mM NaCl, pH 7.0; flow rate (volume per minute of the peristaltic pump): 0.025 ml min$^{-1}$). The dynamic measuring range of the module according to the inventive continuous system showed to be appropriate in a concentration range from 1 to 100 mM (U=−100 mV vs. SCE), with the rotating disk electrode the detection limit is at 1 $\mu$M (200 mV, 25 Hz). The paste may also be imprinted onto a support for mass production (preferably on the electrode material), and be used piece by piece as selective structured layer in order to cover the sensor field. Instead of silicon oil, further bulk materials (compare potentiometric ion-selective membranes) may be used. In order to increase the viscosity and the mechanical ruggedness, an additive, e.g. a polymer such as PVC is incorporated into the silicon oil.

By the example of a phosphate-selective sensor it could be shown, that the preparation of a bienzymatic layer, wherein two enzymes are incorporated within the same layer, is possible [see Müller, J. P.; Entwicklung eines phosphatsensitiven bienzymatischen-ampero-metrischen Biosensors (development of a phosphate sensitive bienzymatic amperometric biosensor) Diploma work ETHZ, 1994]. The phosphate-selective sensing element contains 1 part TTF/TCNQ (tetrathiafulvalene-p-tetracyanoquinodimethane) prepared according to Ferraris et al. [J. Am. Chem. Soc. 95 (1973) 948] in 1.6 parts silicon oil. With this intensively triturated paste e.g. 3.18 wt % xanthine oxidase (EC 1.1.3.2) and 4.35 wt % nucleoside phosphorylase (EC 2.4.2.1) corresponding to 7.53 wt % total lyophilisate concentration are mixed. The paste is deposited into the provided recess (sensor pad) of a modular tube electrode and this is investigated by the arrangement of a rotating disk electrode. The paste is stored at a temperature of −300° C. Before calibration and examination of the electrode, said electrode is conditioned for 16 h in a buffering solution pH 7.0 containing 50 mmol L$^{-1}$ imidazole, 50 mmol L$^{-1}$ sodium chloride and 1.2 mmol L$^{-1}$ inosine. In order to examine the operational conditions, an increment of phosphate solution is added to the pH-buffer, which results in an increase of the phosphate by 1.0 micromol L$^{-1}$ and 5 micromol L$^{-1}$, respectively. The change in the anodic current is measured at a rotation frequence of 25.0±0.05 Hz. The change in concentration was measured at an applied voltage of −50.0±0.2 mV within <15 s.

All three sensor elements introduced herein, may be constructed in the same manner as tube-type electrodes e.g. combined within a single probe in order to be introduced into a reactor or applied in-line linked to the reactor. Each system can comprise several modules of the same type combined with modules of another type. The several modules of identical type may be distinguished by different recognition elements. The processing of the signals, which are derived from the single modules, and the dispatching of the measured results, respectively, is performed according to known procedures. For instance at least one measured quantity can be yielded from one transducer, or a reference quantity can be yielded from the reference module, and be transduced to a device processing the measured quantities, such that the measured quantity can be used to control a process.

The information concerning the substance is obtained e.g. as amount, concentration or concentration change, respectively, as counts, time, activity or active molality.

The system is suitable for the determination of inorganic and organic ions, charged, uncharged or neutral molecules, salts, isotopes, radicals, cells or cell components, organisms, microorganisms, viruses, organellae, or receptors and is applicable in medical diagnosis and treatment, in dialysis and hemodialysis, in clinical analysis, in environmental technology, building technology, clean-room technology, waste water-, ground- and drinking-water surveillance, in food technology and production, in the agriculture, notably in soilless cultures, in food technology, in biotechnology, and in the chemical process control, in the pharmaceutical research and production, the drug technology and the drug control. in the textile technology and in the detergent, cleaning and surfactant technology.

The selective layered structures can be present in very diverse thicknesses. Through the exchangeability they may be easily optimized for specific applications. The caulking between layered structure and sample channel is usually performed by sealing, e.g. from plastic, and by pressing the layered structure with the head piece and the transducing element, respectively, to the seal. The use of selective layered structure enables the operation without reagents. In many cases a dilution and buffering of the specimen is necessary.

What is claimed is:

1. Modular system for the continuous reagent-less determination of at least one substance, said modular system comprising at least two measuring modules of the same or different modular type for the simultaneous yield of at least two items of information during flow-through of said substance, each module including at least one exchangeable selective layered structure and a transducing device cooperating with the layered structure to provide a selective recognition step and allow a continuous measuring of the respective item of information, said selective layered structure being interchangeably sealed in said module by an elasticity of the layered structure, each said module containing a channel for the flow-through of said substance, said channel being in direct communication with said selective layered structure of said module.

2. Modular system according to claim 1, wherein said system is multidimensional and comprises said measuring modules of at least two modular types.

3. Modular system according to claim 1, wherein said measuring modules are selected from the group comprising potentiometric, voltametric, amperometric and optical modules.

4. Modular system according to claim 1, wherein one of said measuring modules is a chemically selective half-cell and a further of said modules is a reference cell.

5. Process for the continuous determination of at least one substance by the modular system according to claim 1, comprising determining at least one measured parameter by said measuring modules in which the selective layered structure of each module allows for a selective recognition step, said recognition step being associated with at least one transduction step leading to the formation of respective said measured parameter, said measured parameter being transduced through at least one transduction device and said transduction of the measured parameter leads at least partially to the information item concerning the substance.

6. Process according to claim 5, wherein at least one transducing device transduces at least one measured parameter from a measuring module or a reference parameter from a reference module onto a device for the transformation of the parameters; such that the resulting information is usable for process control.

7. A method of using the system of claim 1 comprising determining the presence of inorganic and organic ions, charged, uncharged and neutral molecules, salts, isotopes, radicals, cells or cell components, organisms, microorganism, viruses, organellae, or receptors.

8. The method of claim 7 comprising utilizing the system in medical diagnostics and treatment, in dialysis and hemodialysis, or in clinical chemistry.

9. The method of claim 7 comprising utilizing the system in environmental technology, building technology, cleanroom technology, waste water-, ground- or drinking-water surveillance, in textile technology, or in detergent and cleaning and surfactant technology.

10. The method of claim 7 comprising utilizing the system in food technology including food production, in agriculture including soilless cultures, in biotechnology, chemical process control, in pharmaceutical research and production, or in drug technology and drug control.

11. Modular system according to claim 1, wherein said modules are symmetrically disposed in a measuring cell for calibration-free measurements.

12. A method of using the module system according to claim 11 comprising preparing reference materials for the determination of molar activities of ions for quality assessment.

13. Modular system according to claim 35 wherein the selective-layer structure contains a complex of 4,7-diphenyl-1,10-phenanthrolene with ruthenium or lanthanide, lipophilically substituted at the phenyl moiety, for the optical determination of oxygen.

14. A module for use in a modular system for continuous reagent-less determination of at least one substance flowing through said system, said module comprising a replaceable, selective layered structure, a transducing device cooperating with said layered structure for continuously measuring and producing an output signal related to said at least one substance, said selective layered structure having elasticity and being replaceably and sealably secured in said module by said elasticity of the layered structure, said module having a flow-through channel for said at least one substance, said layered structure being in sealed contact with said flow-through channel for flow of said sample therethrough.

15. Module according to claim 14, wherein said layered structure is separated from said transducing device, said transducing device being exchangeable together with or separately from a body of the transducing device.

16. Module according to claim 14, having a counter-electrode, and said flow through channel extending at least partially in the counter-electrode.

17. Module according to claim 14 which is an optical module.

18. Module according to claim 17, wherein said selective layered structure contains at least one ligand selected from the group consisting of disubstituted aminophenyl-4'-trifluoroacetyl-azobenzenes, 4-trifluoroacetyl-4'-(N,N-disubstituted amino) stilbenes and disubstituted p-amino-trifluoroacetylstilbenes.

19. Module according to claim 17, wherein the selective layered structure contains at least one complex of 4,7-diphenyl-1,10-phenanthrolene with ruthenium or lanthanide which is substituted with a lipophilic residue in 4'-position with an alkyl residue.

20. Module according to claim 19, wherein said lipophylic residue is substituted in 4' position and comprises alkyl residue.

21. Module according to claim 20, wherein said lipophylic residue is a propyl to dodecyl residue.

22. Module according to claim 20, wherein said lipophylic residue is a propyl to heptyl residue.

23. Module according to claim 14 wherein the selective-layered structure contains N,N-disubstituted-aminophenyl-4'-trifluoroacetyl-azobenzenes, N,N-disubstituted aminonaphtalene-4'-(N,N-disubstituted-amino) stilbenes and disubstituted-p-amino-trifluoroacetylstilbenes, wherein the substituents are lipohilic, as chromogenic ligands.

* * * * *